US009879813B2

(12) United States Patent
Meola et al.

(10) Patent No.: US 9,879,813 B2
(45) Date of Patent: Jan. 30, 2018

(54) PINCHING DEVICE FOR TEMPORARILY CLOSING FLEXIBLE TUBING

(71) Applicants: Ralph Meola, Fredon, NJ (US); Robert J. Aulicino, Fredon, NJ (US)

(72) Inventors: Ralph Meola, Fredon, NJ (US); Robert J. Aulicino, Fredon, NJ (US)

(73) Assignee: BIO FLEX SOLUTIONS, LLC, Hackettstown, NJ (US)

( * ) Notice: Subject to any disclaimer, the term of this patent is extended or adjusted under 35 U.S.C. 154(b) by 466 days.

(21) Appl. No.: 14/155,306

(22) Filed: Jan. 14, 2014

(65) Prior Publication Data

US 2015/0198272 A1    Jul. 16, 2015

(51) Int. Cl.
*F16L 15/08* (2006.01)
*F16L 55/10* (2006.01)
*B25B 5/10* (2006.01)

(52) U.S. Cl.
CPC .............. *F16L 55/10* (2013.01); *B25B 5/103* (2013.01); *Y10T 24/44265* (2015.01)

(58) Field of Classification Search
CPC .................................. A44B 11/06; B25B 5/04
USPC ........ 24/486, 517, 132 WL, 514; 81/DIG. 9; 72/481.6; 251/9; 606/120; 604/250
See application file for complete search history.

(56) References Cited

U.S. PATENT DOCUMENTS

| 788,603 | A | | 5/1905 | Rowell |
| 1,987,159 | A | * | 1/1935 | Rasmussen .................... 206/388 |
| 2,215,122 | A | * | 9/1940 | Hess .................................. 81/6 |
| 2,686,520 | A | * | 8/1954 | Jarvis et Al .................. 606/120 |
| 3,203,421 | A | | 8/1965 | Bialick |
| 3,247,852 | A | | 4/1966 | Schneider |
| 4,091,815 | A | | 5/1978 | Larsen |
| 4,363,388 | A | * | 12/1982 | London et al. .................. 383/23 |
| 4,978,100 | A | * | 12/1990 | Peurifoy ........................... 251/8 |
| 5,018,768 | A | * | 5/1991 | Palatchy ......................... 285/24 |
| 5,864,927 | A | * | 2/1999 | Liu ............................ 24/163 R |
| 7,137,611 | B2 | * | 11/2006 | Aulicino ........................... 251/9 |
| 7,559,525 | B2 | | 7/2009 | Grimes |
| 2005/0278906 | A1 | * | 12/2005 | Moncavage ....... A44B 11/2569 24/517 |
| 2007/0102658 | A1 | * | 5/2007 | Grimes ............................. 251/9 |
| 2013/0011201 | A1 | * | 1/2013 | Gutierrez et al. ............ 405/170 |

\* cited by examiner

*Primary Examiner* — Robert Sandy
*Assistant Examiner* — Matthew J Sullivan
(74) *Attorney, Agent, or Firm* — Francis C. Hand; Carella, Byrne, et al

(57) ABSTRACT

The pinching device has an upper jaw assembly that pivots on a lower jaw assembly to clamp a flexible tubing between two clamping surfaces to restrict flow in the tubing. The upper jaw assembly is removable and may be replaced to accommodate different sized tubing. A lock down screw of a pivotal locking nut assembly is positioned in a compression seat of the upper jaw assembly at closure to avoid movement once set.

5 Claims, 5 Drawing Sheets

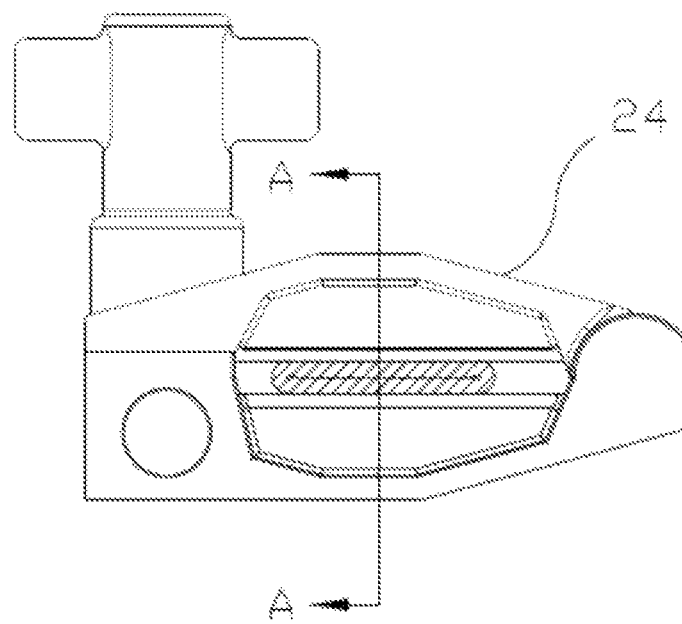
FIG. 4
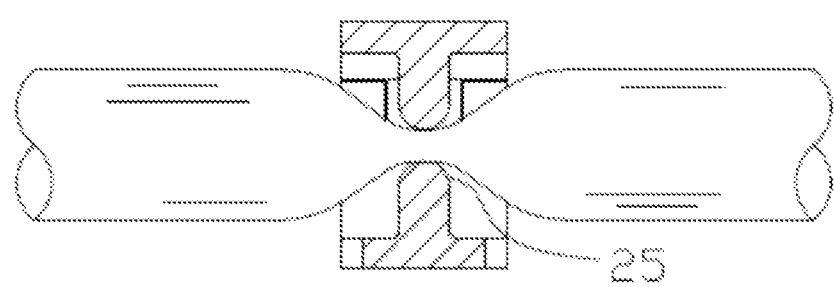
SECTION A-A

PINCHING DEVICE FOR TEMPORARILY CLOSING FLEXIBLE TUBING

This invention relates to a pinching device and more particularly to a pinching device for temporarily closing flexible tubing.

BACKGROUND OF THE INVENTION

Devices of this nature are used in the food and pharmaceutical industry for temporary closure of fluid lines. Typically, pinching devices are used for specific size of tubing, most require tubing to be inserted prior to connection. An example, similar but with difference, is described in U.S. Pat. No. 7,559,525.

In many circumstances, it is desired to install closure devices without the need to insert tubing through the device, thereby allowing the device to be placed at various locations along fluid lines while actively in use. While many closure devices exist, most service smaller tubing sizes and are not designed substantial enough for the larger fluid lines. There is a need for an improved version that offers security and ease of installation.

From prior art, there also is no offering of interchangeable jaw members applicable to a wider range of tubing sizes.

SUMMARY

The invention allows improved clamping of larger tubing and hose assemblies utilized predominately in the pharmaceutical industry, without the need to expose fluid process lines to potential contamination. This is accomplished with a device that is comprised by two members that may pivot thereby allowing an upper member to compress onto the lower fixed member. Once closure has been accomplished both members may be locked into place by a special locking member.

A swing away locking member allows a screw to clear a compression seat with a minimum amount of turns, which will be of ergonomic value to operators.

It is also the intent of the device to be manufactured with nonmetallic inexpensive materials. The device may be reusable or deemed disposable which is a function of its application.

With a variety of tubing clamps presently available, the largest portion of these devices are designed for smaller tubing. Primarily this type of tubing which is silicone, but not limited to, is utilized in pharmaceutical and food applications. An example of tubing restrictors may include hemostats along with a variety of clamps for the purpose of restricting flow. Many fluid restrictive devices require clamps to be installed prior to assembly thus not removable once installed and operational. Many clamping devices are also configured which may cause damage to outer surface of tubing or hose.

In addition to stopping or restricting flow, the device is suitable to be utilized at various termination points. This also eliminates the need to have a permanent closure end connections until assemblies have been completed for final assembly.

It is also the intent of the invention to be produced in materials capable of sterilization by autoclaving or gamma exposure.

DRAWING DESCRIPTION

FIG. 4 illustrates a cross section of the device in contact with tubing during closure.

DETAIL DESCRIPTION OF DEVICE

The drawings contained herein make reference in numerical notations as to the make up of the invention and claims associated.

Figure 1:
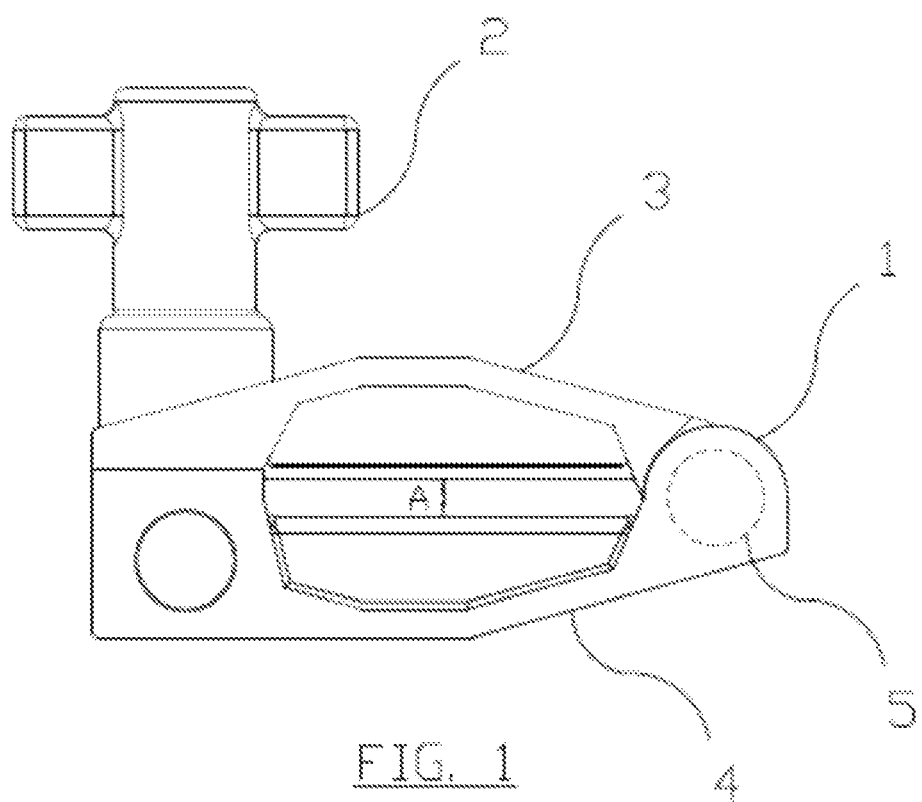
FIG. 1 is a side elevation of the device in the closed and locked position.

Referring to FIG. 1, the pinching device is a sanitary tube clamp 1 of a nonmetallic construction having an upper jaw assembly 3 pivotally mounted on a lower jaw assembly 4 about a pivot point 5 and secured in place by a locking nut assembly 2.

Figure 3:
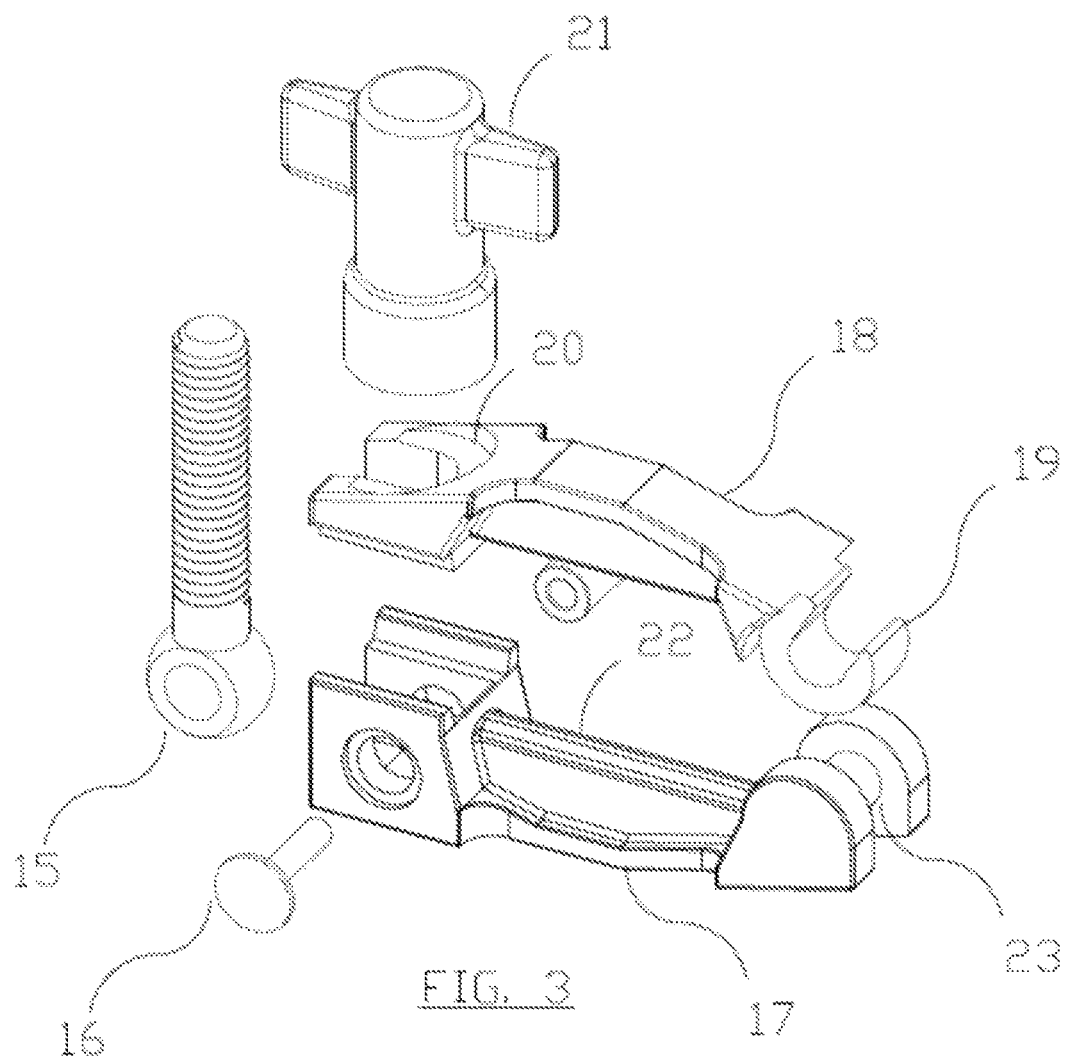
FIG. 3 illustrates an exploded of the invention illustrating all components that make up the assembly.

Referring to FIG. 3, the upper jaw assembly 3 has an arm member 18 with a hook segment 19 at one end while the lower jaw assembly 4 has an arm member 17 has a pivot 23 that receives the hook segment 19.

The construction of the jaw assemblies 3, 4 allows for interchangeable members.

An end pivot section of the upper jaw assembly may also be configured to limit travel of the arm member 18 arm to a specific rotation by being fitted onto the stationary pivot 23.

The upper and lower arm members 18, 17 in the closed position regulate a fixed closure gap "A" (see FIG. 1) to compress tubing to restrict or stop fluid path. The design gap is configured to restrict flow in tubing or hose with a range of wall thickness of from 0.085 to 0.193 inches.

The clamping surface of each arm member 17, 18 is configured with a rounded cross section of contact area (see FIG. 4 Section A-A). The working surface of the pinching member is approximately 1.625 inches length in order to allow clearance for tubing or hose in the closed size range. The device clamp members are constructed in a manner to avoid damage to walls of the tube or hose being subjected to restriction.

In addition, the pivot point of the pinching device is offset as to allow parallel clamping to a tube or hose.

The arm members serve as clamping members with pinching bars offset from the main body of the members to provide pressure to tube or hose for closure.

Item 3 is considered the latching member while item 4 is the retaining member.

As the locking nut assembly 2 is secured, the fluid path may be metered or stopped in order perform various operations to fluid lines.

Figure 2:
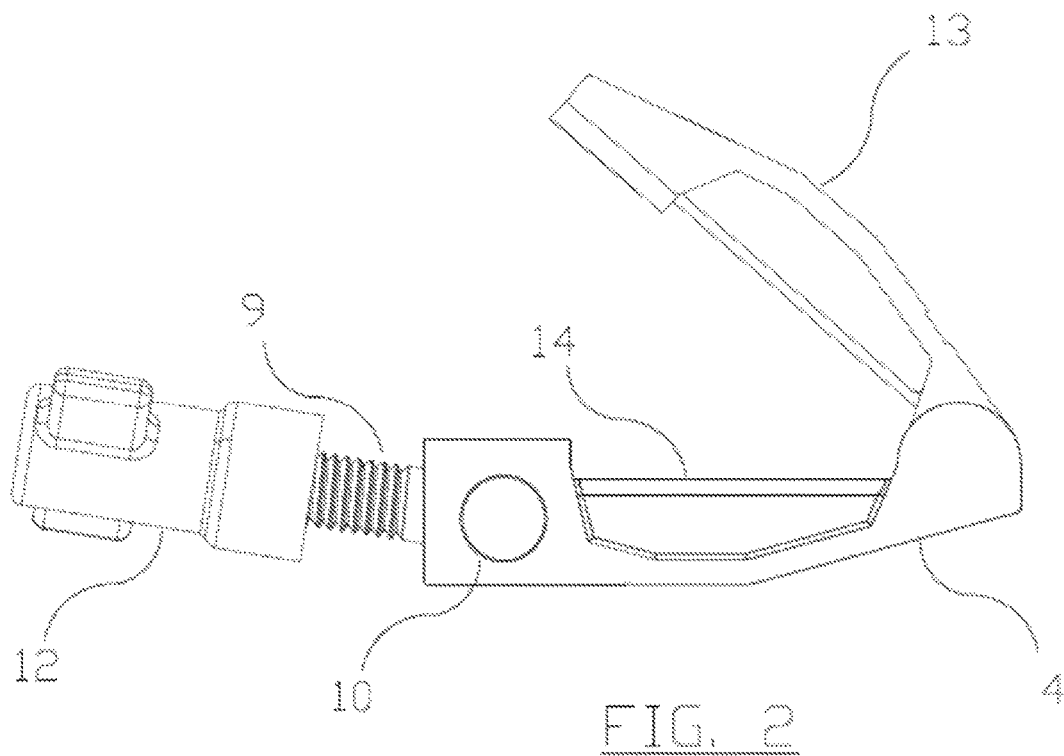
FIG. 2 illustrates the invention in the open and swing away position thereby releasing the device from its closure position.

Referring to FIG. 2, wherein the clamp 1 is in the unlocked and open position, the locking nut assembly 2 is in an open position to release pressure from the tubing and or removal.

Referring to FIG. 3, the locking nut assembly 2 is in the form of a two part pin assembly, formed of an elongated cylindrical threaded pin 15 and a lock nut 21. The threaded pin 15 is pivotally attached to the arm member 17 of the lower jaw assembly 4 by means of a pivot pin 16 and the lock nut 21 is received in a compression seat 20 at one end of the upper arm member 18.

The geometries on the lock nut 21 surface and the surface of the compression seat 20 that engage upon closure are such as to emit an audible and physical indicator that closure has been accomplished. Having friction between the tightening nut and compression seat surface will also prevent loosening of the jaws by engaging the design surface area. The jaws in turn limit the travel in correspondence with the pinch surfaces.

The compression seat is designed to encapsulate up to 260 degrees of the locking nut 21 when tightened in order to have the locking nut 21 remain in lock down and in a generally perpendicular position to the jaws until nut 21 is rotated to be loosened. This results in the elimination of any movement in the closed position.

The compression seat 20 serves to capture the locking nut 21 which imparts radial compression to the seat surface as the locking nut 21 is secured.

Referring to FIG. 2, after the locking nut 21 is loosened and the locking nut assembly 2 swung free of the compression seat 20, the upper member 13 may be opened. Item 14 illustrates the rounded design of the upper and lower matching jaws.

With a minimum rotation, the locking nut assembly 2 may swing clear of retaining the upper jaw for removal of a tube.

Referring to FIG. 3, the pivot pin 16 is comprised of a male and female embodiment. To ensure integrity of the assembly, pivot pin 16 is pressed into lower member 17.

The upper 18 and lower 17 members have been segmented in a designed configuration for strength and light weight. The upper member 18 is attached to lower assembly by the hook segment 19. The lower member 17 is configured to receive pivoting hook segment onto the mating pivot 23. The upper member 18 may be configured in two versions to accommodate various tube or hose sizes. The upper member 18 also represents the compression seat 20 which captures the locking nut 21 within the confines on the compression seat. The upper and lower jaws 22 incorporate rounded smooth surface areas 14 to prevent damage to tubing or hose.

FIG. 4 illustrates an alternate standard upper jaw item 24 used for tubing with a wall thickness range of 0.085 to 0.193. Alternate jaw used for smaller tubing sizes will range from 0.025 to 0.085 wall thickness.

Section A-A of FIG. 4 illustrates rounded clamping areas 25 subjected to surface of tubing. The jaw surfaces have been configured for maximum pressure against tubing or hose to allow for complete restriction under normal operating pressures.

Figure 5:
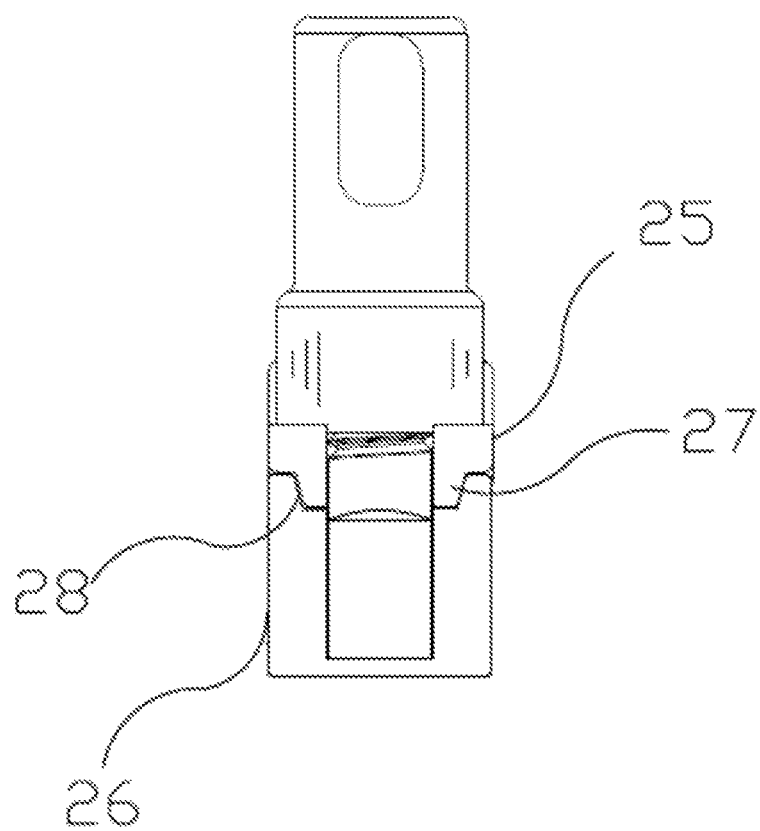
FIG. 5 illustrates a front view of the device in the closed and locked position.

FIG. 5 shows a front view of the device in the closed and locked position illustrating the interlocking upper jaw 25 and lower jaw 26. The extended geometry on the upper jaw 27 and the mating recess 28 on the lower jaw restricts the jaws from any side movement once the members have been seated while aligning the members into a closed position.

The interlocking jaws at closure add to the integrity of the locking mechanism and restricts the jaws from any side movement once the members have been seated also aligning the members to a closed position and limiting travel of the jaws.

The pinching device is capable of sterilization by standard methods associated with provisions set forth by the pharmaceutical regulatory standards. This can also include but not be limited to steam, autoclaving, or gamma sterilization.

The device is configured to accommodate various larger flexible tubing and hose.

The device employs a quick change jaw assembly and a material impervious to most chemicals.

The pinching device is used as a simple and manual means of controlling fluid through flexible tubing or hose. Most common tubing and hose material is silicone, copolymer and TPE materials.

The invention claimed is:

1. A pinching device comprising
   a lower jaw assembly having a first rectilinear pinching bar and a pivot at one end of said pinching bar;
   an upper jaw assembly having a second rectilinear pinching bar opposite said first rectilinear pinching bar for pinching a flexible tube therebetween, a hook portion at one end of said second rectilinear pinching bar received on said pivot of said lower jaw assembly, a bifurcation at an opposite end of said second rectilinear pinching bar and a recessed seat in an upper surface at said opposite end thereof; and
   a locking nut assembly having a threaded pin pivotally mounted on an end of said lower jaw assembly opposite said one end of said first pinching bar and releasably disposed in said bifurcation of to said upper jaw assembly and a nut threaded on said pin and seated within said recessed seat.

2. A pinching device as set forth in claim 1 wherein said lower jaw assembly has a recess receiving said upper jaw assembly in mating relation to restrict said upper jaw assembly from side movement relative to said lower jaw assembly.

3. A pinching device as set forth in claim 1 wherein said first rectilinear pinching bar has a rounded clamping surface facing said second rectilinear pinching bar and said second rectilinear pinching bar has a rounded clamping surface facing said first rectilinear pinching bar to define a gap therebetween.

4. A pinching device as set forth in claim 1 wherein said upper jaw assembly is configured to limit travel thereof on said pivot of said lower jaw assembly.

5. A pinching device comprising
   a lower jaw assembly having a first rectilinear pinching bar and a pivot at one end of said pinching bar;
   an upper jaw assembly having a second rectilinear pinching bar opposite said first rectilinear pinching bar for pinching a flexible tube therebetween,
   a hook portion at one end of said second rectilinear pinching bar removably received on said pivot of said lower jaw assembly, a bifurcation at an opposite end of said second rectilinear pinching bar and a recessed seat in an upper surface at said opposite end thereof; and
   a locking nut assembly having a threaded pin pivotally mounted on an end of said lower jaw assembly opposite said one end of said first pinching bar and releasably disposed in said bifurcation of to said upper jaw assembly and a nut threaded on said pin and seated within said recessed seat.

* * * * *

UNITED STATES PATENT AND TRADEMARK OFFICE
CERTIFICATE OF CORRECTION

PATENT NO. : 9,879,813 B2
APPLICATION NO. : 14/155306
DATED : January 30, 2018
INVENTOR(S) : Ralph Meola et al.

Page 1 of 1

It is certified that error appears in the above-identified patent and that said Letters Patent is hereby corrected as shown below:

Column 4, Line 26, cancel "to"
Line 57, cancel "to"

Signed and Sealed this
Twenty-ninth Day of May, 2018

Andrei Iancu
*Director of the United States Patent and Trademark Office*